United States Patent [19]

Krull et al.

[11] Patent Number: 5,449,918
[45] Date of Patent: Sep. 12, 1995

[54] AMPLIFIED FLUORESCENCE EMISSION FOR CHEMICAL TRANSDUCTION

[75] Inventors: Ulrich J. Krull, Mississauga; Reno F. DeBono, Toronto, both of Canada

[73] Assignee: Her Majesty the Queen in Right of Canada, as represented by The Minister of National Defence of her Majesty's Canadian Government, Canada

[21] Appl. No.: 109,524

[22] Filed: Aug. 20, 1993

[30] Foreign Application Priority Data

Aug. 24, 1992 [CA] Canada .................... 2076709

[51] Int. Cl.⁶ ............................................ G01N 21/64
[52] U.S. Cl. ............................ 250/458.1; 250/459.1
[58] Field of Search ......................... 250/458.1, 459.1

[56] References Cited

PUBLICATIONS

P. Rouard et al. "Optical properties of . . . " I: Wolfe Progress in Optics VX North-Holland 1977, pp. 79–132.
D. A. Weitz et al. "The enhancement of Raman scattering, . . . " J. Cehm. Phys. 7819, 1 May 1983, pp. 5324–5338.
D. A. Weitz et al. "Excitation spectra of . . . " Optics Letters, vol. 7 No. 4, Apr. 1982, pp. 168–170.
J. Gerstern, "Spectroscopie properties . . . " J. Chem. Phys., vol. 75 No. 3, 1 Aug. 1981.
I. Pockrand et al. "Surface Plasmon . . . " Surface Science 4(19) 1977, pp. 237–244.
W. H. Weber et al. "Energy transfer . . . " Optics Letter, vol. 4 No. 8 Aug. 1979.
I. Pockrand et al. "Nonradiative decay of excited . . . " Chemical Physics Letter, vol. 69 No. 3, 1 Feb. 1980, pp. 499–504.
F. R. Aussenegg et al. "Novel Aspects of fluorescence . . . " Surface Science 189/190 (1987), pp. 935–945.
A. Wokaun et al. "Energy transfer in surface . . . " J. Chem. Phys., vol. 79 No. 1, Jul. 1983, pp. 535–515.
J. D. Brennan et al. "Hydronium ion sensitivity . . . " Thin Solid Films, 203 (1991) pp. 173–184.

*Primary Examiner*—Paul M. Dzierzynski
*Assistant Examiner*—Richard Hanig
*Attorney, Agent, or Firm*—Nixon & Vanderhye

[57] ABSTRACT

A novel optical chemical sensor for direct and continuous detection of organic species in process streams is described. The sensor is based on the use of surface plasmon resonance to amplify fluorescence emission from chemically selective membranes which can be deposited as Lang-muir-Blodgett films on thin metal island films.

8 Claims, 16 Drawing Sheets

Fig. 2

| Surface wettability properties | Configuration of deposited layers | Distance of fluorophore from substrate interface | Distance of fluorophore from air interface |
|---|---|---|---|
| hydrophilic<br>-glass<br>-Ag Island<br>A-I, A-II,<br>B-II | | 4-5 Å | 30 Å |
| hydrophobic<br>-silver film<br>-Ag Island<br>A-II, B-II | | 30-35 Å | 30 Å |

Fig. 8

| Ag ISLAND FILM TYPE | A-I | A-II | B-I | B-II |
|---|---|---|---|---|
| DEPOSITION CONDITIONS<br>SUBSTRATE TEMP. (°C)<br>MASS THICKNESS (Å)<br>DEPOSITION RATE (Å/sec) | 25<br>40<br>0.6 | 25<br>40<br>0.6 | 200<br>40<br>0.6 | 25<br>40<br>0.6 |
| WETTABILITY | hydrophilic | variable | hydrophilic | hydrophobic |
| SEM ANALYSIS<br>SURFACE COVERAGE (%)<br>PARTICLE DENSITY (#/μm²)<br>AVERAGE DIAMETER (Å)<br>AVERAGE SHAPE FACTOR | 57±9<br>1000±100<br>240±100<br>1.3±0.3 | 68±8<br>1200±150<br>220±90<br>1.7±0.8 | 68±9<br>2400±150<br>160±50<br>1.2±0.3 | 68±9<br>2400±150<br>160±50<br>1.2±0.3 |

Fig. 9

| | 0.1% NBD-PE/BA | 1.0% NBD-PE/BA |
|---|---|---|
| SILVER ISLAND A-II | 1±1 | 18±1, 13±1* |
| SILVER ISLAND B-I | 0±1 | 2±1 |
| SILVER FILM* | 0±0* | 0±0* |

Fig. 10

| | NBD | | TRITC | |
|---|---|---|---|---|
| | EXCITATION 450 nm | PEAK EMISSION 534 nm | EXCITATION 510 nm | PEAK EMISSION 566 nm |
| $\varepsilon_1$ | −7.1 | −11.6 | −10.5 | −14 |
| $\varepsilon_2$ | 0.23 | 0.36 | 0.32 | 0.40 |
| $(\varepsilon_1^2 + \varepsilon_2^2)$ | 50 | 135 | 110 | 196 |
| FIELD INTENSITY ENHANCEMENT | A-II - 1900<br>B-I - 3200 | A-II - 2300<br>B-I - 4000 | A-II - 2700<br>B-I - 4200<br>B-II - 4300 | A-II - 3000<br>B-I - 6800<br>B-II - 4100 |

AMPLIFIED FLUORESCENCE EMISSION FOR CHEMICAL TRANSDUCTION

FIELD OF THE INVENTION

This invention relates to a novel optical chemical sensor based on the use of metal island films to modify and/or amplify the fluorescence signal obtained from chemically selective membranes on or near these metal island films.

Background of Invention

Sensors that are capable of reliable, selective and sensitive detection of organic species and functional groups are highly desirable for incorporation into conventional spectrophotometers. Fluorescence has been adopted as the spectroscopic technique of choice for optical sensor development due to its sensitivity and the opportunity for simultaneous multidimensional analysis using parameters of wavelength, intensity, polarization and lifetime. In combination these analytical parameters can be used to define unique solutions to both the qualitative and quantitative aspects of analysis. These techniques are useful for the direct and continuous detection of organic species in process streams-such as effluent streams.

Two problems associated with fluorescence spectroscopy as a strategy for the transduction of selective binding interactions is the relatively small absolute intensity that is available and the inability to use smooth metal substrates. Efforts have been made to overcome the weak signal using ultrasensitive detection equipment, powerful pulsed lasers, and by signal integration over extended periods of time. Such solutions however are costly and have tended to limit the potential for development of sensitive, small, low cost chemical sensors based on fluorescence spectroscopy. The fluorescence quenching effects of metal films has prevented the use of metals in conjunction with fluorophores for the facile self-assembly of rugged ultrathin chemically selective organic layers [1].

Metal island films composed of randomly distributed particles whose dimensions are small compared to the wavelength of visible light exhibit absorption bands in the visible region of the electromagnetic spectrum [2] as a result of the collective oscillation of conduction band electrons(surface plasmons). Metal island films can be used to enhance the analytical signal available from chemically selective membranes utilizing a fluorescence transduction scheme and can form the basis for the self-assembly of ultrathin organic films at surface.

Basis of interaction:

A molecular fluorophore can be modeled [3] as a four-state system consisting of two electronic states $S_o$ and $S_1$ which each contain two vibrational levels, a zero-point and an excited state (*). The relative energy levels of these states are $S_o < S_o^* < S_1 S_1^*$. Molecular fluorescence involves the absorption of a photon and the promotion of an electron from the ground state $S_o$ to the excited state $S_1^*$, followed by thermal relaxation(-transfer) to state $S_1$ and then radiative emission to the vibrationally excited ground state $S_o^*$. The fluorescence yield (F) of the system is a function of the absorption rate ($\Omega$), the transfer yield ($Y_{trans}$) and emission yield ($Y_{em}$) as shown in equation 1.

$$F = \Omega Y_{trans} Y_{em} \tag{1}$$

The absorption rate is indicative of the rate at which the excited state is populated and is a function of the cross-section of capture ($\sigma$) of the fluorophore times the square of the local electric field strength ($E_{local}^2$).

$$\Omega = \sigma E_{local}^2 \tag{2}$$

The effective population of the vibrationally relaxed excited electronic state $S_1$ is characterized by the transfer yield, which is the ratio of the thermalization rate ($T_{S_1^*}$) (from state $S_1^*$ to state $S_1$) to the total relaxation rate of $S_1^*$.

$$Y_{trans} = \frac{T_{S_1^*}}{T_{S_1^*} + (\Gamma_{S_1^*}^R + \Gamma_{S_1^*}^{NR})} \tag{3}$$

The total relaxation rate from state $S_1^*$ is the sum of the thermalization rate ($T_{S_1^*}$) and the electronic radiative (R) and nonradiative (NR) relaxation rates ($\Gamma_{S_1^*} = \Gamma_{S_1^*}^R + \Gamma_{S_1^*}^{NR}$).

The emission yield of state $S_1$ is the ratio of the radiative decay rate to the sum of all the radiative and nonradiative decay rates from state $S_1$.

$$Y_{em} = \frac{\Gamma_{S_1}^R}{\Gamma_{S_1}^R + \Gamma_{S_1}^{NR}} \tag{4}$$

This value is indicative of the quantum yield of the emitting state and is always smaller than or equal to 1.

An evanescent electric field is produced at the surface of a small metal particle such as silver, gold, indium, or alloys of mixtures of said metals which is significantly enhanced over that of the incident field, as a result of the coherent motion of electrons associated with the surface plasmon. The electric field enhancement surrounding a nonspherical particle is not uniform and depends on the shape of the particle. This enhancement, however, will be most intense in regions of high curvature. A phenomenological relationship developed by Weitz et al. [4] relates the fraction of light absorbed, $A(\lambda)$, at wavelength $\lambda$ (in vacuum), by the island film to the average field enhancement (f) at the particle surface as $$f^2(\lambda) = \frac{\lambda}{2\pi q t \epsilon_2} A(\lambda)(\epsilon_1^2 + \epsilon_2^2) \tag{5}$$

where q is the volume fraction of the film, t the film thickness $\epsilon_1 + i\epsilon_2$ is the bulk complex dielectric constant of silver metal particles in the visible electromagnetic spectrum and $\epsilon_1 < 0, \epsilon_2 >$ and $|\epsilon_1| < \epsilon_2$. The local electric field intensity decreases with distance (d) from a spherical particle [5] of radius (r) as $$(E_{local})^2 \propto \left[\frac{r}{r+d}\right]^6 \tag{6}$$

When a fluorophore is located within approximately two particle diameters of a metal island [6] and its absorption and fluorescence bands overlap the absorption band of the metal island film, the fluorophore will then experience a large electric field amplification at the excitation and emission wavelengths. If $f_{\lambda ex}$ and $f_{\lambda em}$ are the enhancement factors associated with the electric field at the excitation and emission wavelengths respectively then the absorption rate is given by:

$$\Omega = \sigma_{\lambda ex}^2 f_{\lambda ex}^2 E_{inc}^2 \qquad (7)$$

and similarly the radiative emission rate is enhanced over the spontaneous emission rate ($\Gamma_{spont}^R$) as $$\Gamma^R = f_{\lambda em}^2 \Gamma_{spont}^R \qquad (8)$$

Close proximity of the fluorophore to the metal surface provides an alternative non-radiative relaxation mechanism resulting in the production of electron-hole pairs or surface plasmons, which can increase the non-radiative decay rate of the fluorophore. This non-radiative energy transfer process involves dipole-dipole interactions which are described by a Forester-energy transfer process. As a result, the non-radiative relaxation rate depends on the distance of the fluorophore from the surface of the metal, and on the overlap of the fluorescence emission profile of the fluorophore and the absorption profiles of the island metal film. The non-radiative decay rate has been predicted to decreases with distance (d) from the surface [5] approximately as $$\Gamma^{NR} \propto \frac{1}{d^3} \qquad (9)$$

The subsequently (electronically) excited state of the metal particle can relax radiatively or non-radiatively. For small particles (r<150 Å) [6] resistive heating (Joule heating) as a result of fluctuating electric fields within the metal island provides a significant non-radiative decay channel. Hence by controlling the particle size the type of signal which is to be measured (heat or fluorescence emission) can be optimized.

OBJECT OF INVENTION

The object of this invention is to enhance the measured signal associated with fluorophores in a chemically selective membrane by the deposition of said membrane onto a metal island film. The metal island film consists of particles with dimensions smaller than the wavelength of visible light deposited on a solid substrate such as glass.

BRIEF STATEMENT OF INVENTION

By one aspect of this invention there is provided an optically based chemical sensor comprising a substrate, a metal island film deposited on said substrate, and a film which contains a fluorescent species deposited on or near said metal island film, where signal enhancement of said sensor is achieved when an excitation wavelength of an excitation source overlaps an absorption profile of said fluorophore and said metal island film.

BRIEF DESCRIPTION OF DRAWINGS

FIG. 7a is the integrated normalized fluorescence response for glass substrate, FIG. 7b is the background corrected fluorescence spectra for glass substrate, FIG. 7c is the integrated normalized fluorescence response for silver island substrate and FIG. 7d is the background corrected fluorescence spectra for silver island substrate.

FIG. 8 is a tabular summary of the deposition conditions, wetability and morphological characteristics of the indicated silver island film types.

FIG. 9 is a tabular summary of the integrated fluorescence intensity of 0.1 and 1 mol % NBD-PE/BA layers deposited on silver island types A-II and B-I and a smooth silver film.

FIG. 10 is a tabular summary of calculated approximations of the field intensity enhancements for the indicated excitation and emission wavelengths.

DETAILED DESCRIPTION OF PREFERRED EMBODIMENTS

Figure 1:
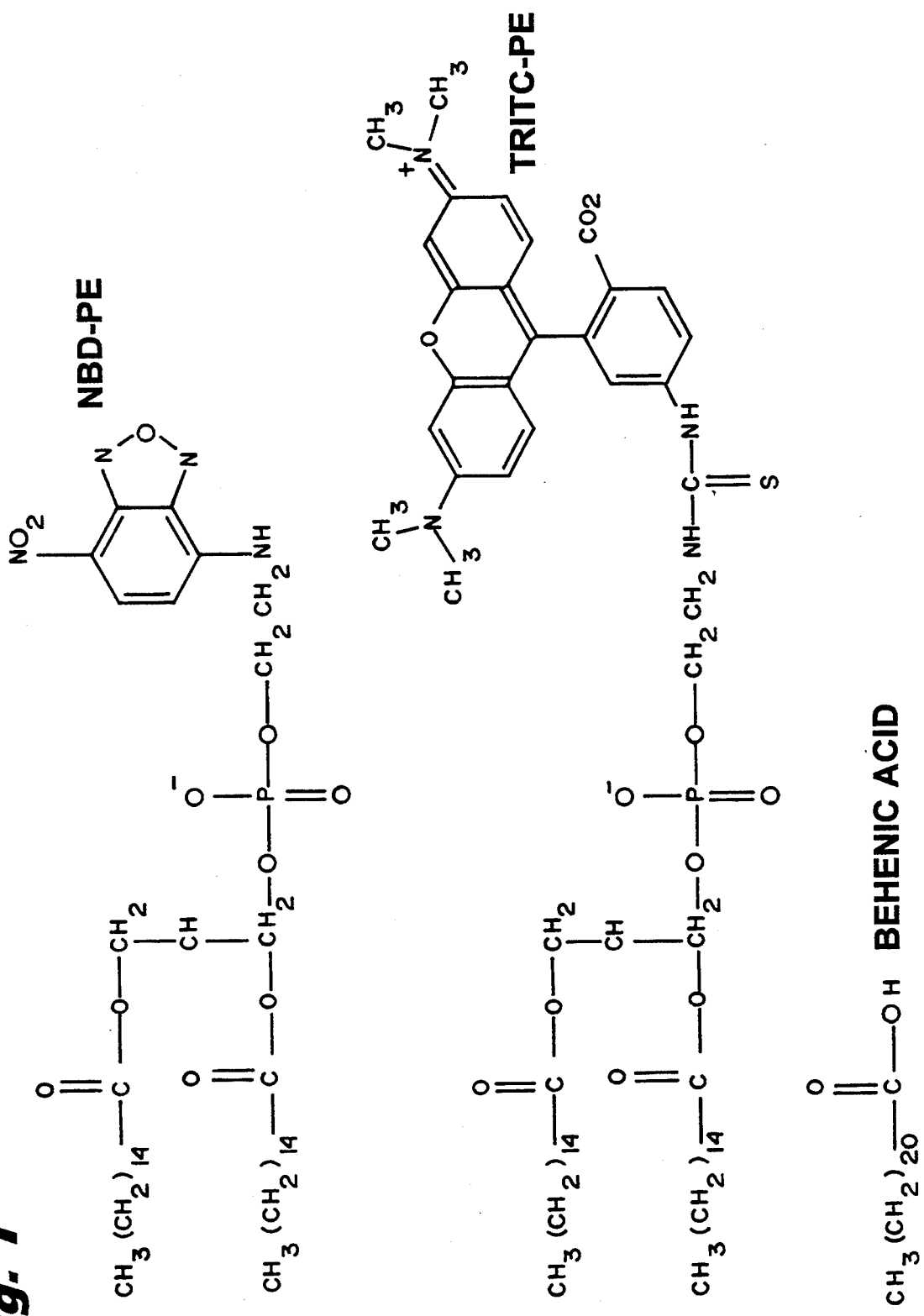
FIG. 1. A sketch illustrating the molecular structures of NBD-PE, TRITC-PE and Behenic Acid FIG. 2. A table illustrating the average distance of fluorophore from the substrate and air interface.

The use of silver island films in the design and construction of fluorescently based sensors was examined in conjunction with the fluorophores nitrobenzoxadiazole (NBD) and 6-tetramethylrhodamine-thiocarbamoyl (TRITC) which were covalently attached at the head group of the lipid dipalmitoyl-L-phosphatidyl-ethanolamine (PE). Behenic acid (BA) monolayers containing 0.1 to 1 mol % of each fluorophore were deposited by Langmuir-Blodgett (LB) techniques onto 40 Å thick silver island films and 1600 Å thick smooth silver film. The structures of NBD-PE, TRITIC-PE and BA are illustrated in FIG. 1. Fluorescence was observed for both NBD and TRITC films which were deposited onto silver island films with average island diameters greater than 200 Å. Very little or no fluorescence was observed for systems with island diameters less than 200 Å and no fluorescence was observed from smooth silver films. The fluorescence response resulting from structural changes in a 1 mol % NBD-PE/BA monolayer deposited on a glass surface and a bilayer deposited on a silver island surface induced by exposure to water vapour and a mixture of water and acetic acid vapour was examined. Both systems responded in a reproducible and reversible manner upon hydration but an amplified fluorescence response was observed for the silver island surface. Partitioning of acetic acid into the bilayer on the silver island surface further amplified the fluorescence response to hydration.

SAMPLE PREPARATION

Wafers were sonicated in hot detergent for 30 minutes and washed in distilled water. They were then soaked in sulfochromic acid for 5 minutes, rinsed with copious quantities of distilled water and then dried in an oven at 90° C. for at least 2 hours. Silver island films with a mass thickness of 40 Å were vacuum evaporated onto cleaned microscope slides at a rate of 0.6 Å/s, and were prepared either with the substrate at room temperature or while maintaining the substrate at 200° C. through the use of a block heater. A smooth 1600 Å silver film was then deposited at a rate of 26 Å/s on the back of the silver island film or on one side of a non-coated glass slide. This configuration permitted ellipsometric analysis of the smooth silver side, reflectance absorption measurements of the silver island side and most importantly, prevented fluorescence from the opposite face from being measured.

A 1 mg/ml solution of BA in chloroform/methanol (3/1; v/v) was prepared. A mixture of 0.1 mol % and 0.5 mol % TRITC-PE to BA were prepared by addition of the appropriate volume of 32 μM TRITC-PE (MW=1237 g/mol) in methanol to the BA solution. Mixtures of 0.1 mol % and 1 mol % solutions of NBD-PE to BA were prepared by the addition of the appropriate volume of 1 mg/ml NBD-PE (MW=854 g/mol) in ethanol solution to the BA solution. All solutions were stored at −20° C. in capped vials and sonicated for 5 min at room temperature before use.

A subphase of 0.1 mM of $CdCl_2$ in Milli-Q was used to prepare monolayers from the NBD-PE/BA and TRITC-PE/BA solutions. Small amounts (110 to 180 μl) of the solutions were slowly spread over 1000 $cm^2$ of the surface of the subphase and then were allowed to equilibrate for 25 min. One cycle of compression-expansion-compression was carried out at a speed of 15 $cm^2$/min. The film was then allowed to stabilize for 45 min at a constant pressure of 33 mN/m. Dipcasting of the monolayers onto the solid substrate was performed at a rate of 0.5 $cm^2$/min and at a constant pressure of 33 mN/m.

Gas phase experiments were carried out in three configurations: A) dry argon flow directly to gas cell, B) argon flow bubbled through distilled water to obtain 30 ppt water vapour and C) argon flow bubbled through a 1:10 mixture of acetic acid/water(v/v) solution to obtain a gas mixture of 30 ppt water and 0.5 ppt acetic acid vapour. The gas cell consisted of a cylindrical quartz tube with a flow inlet at the top and an outlet at the bottom which was placed inside the fluorescence spectrometer in such a way that the wafer could be inserted from the top. Wafers were exposed to a gentle gas flow for two minutes and then the fluorescence spectrum was recorded under static conditions. For configurations B and C the humidity was 80 to 90% while with pure argon a humidity reading of 10% was obtained. The system was at an ambient temperature of 22.5°±0.5° C.

RESULTS

Figure 4A:
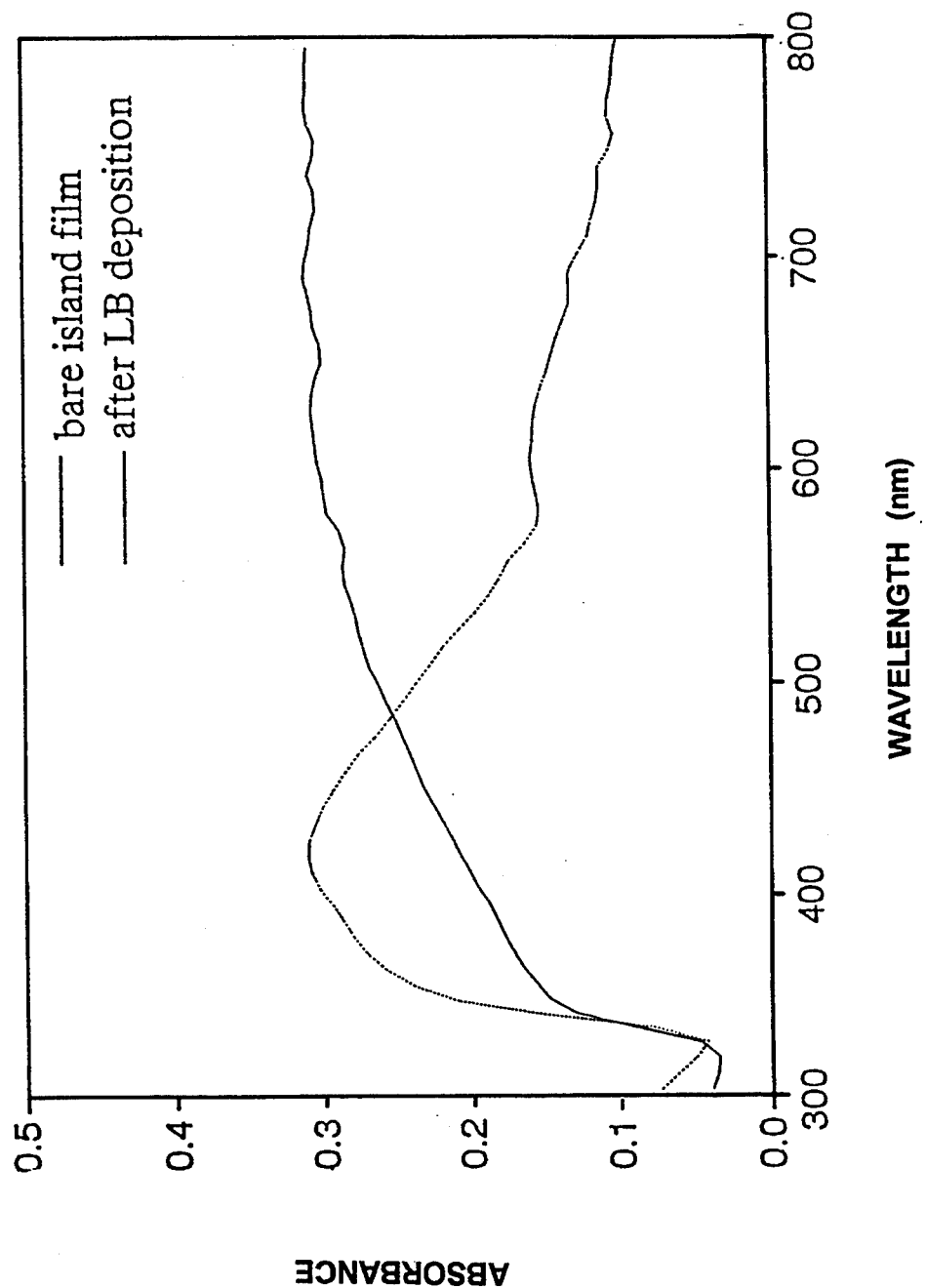
FIGS. 4a, 4b, 4c and 4d are absorbance spectra obtained from reflectance spectra ($\Theta_{inc}=45°$) of 40 Å mass thickness silver island films before and after LB deposition of behenic acid layers for silver island film type A-I, silver island film type A-II, silver island film type B-I and silver island film type B-II respectively.
Figure 4B:
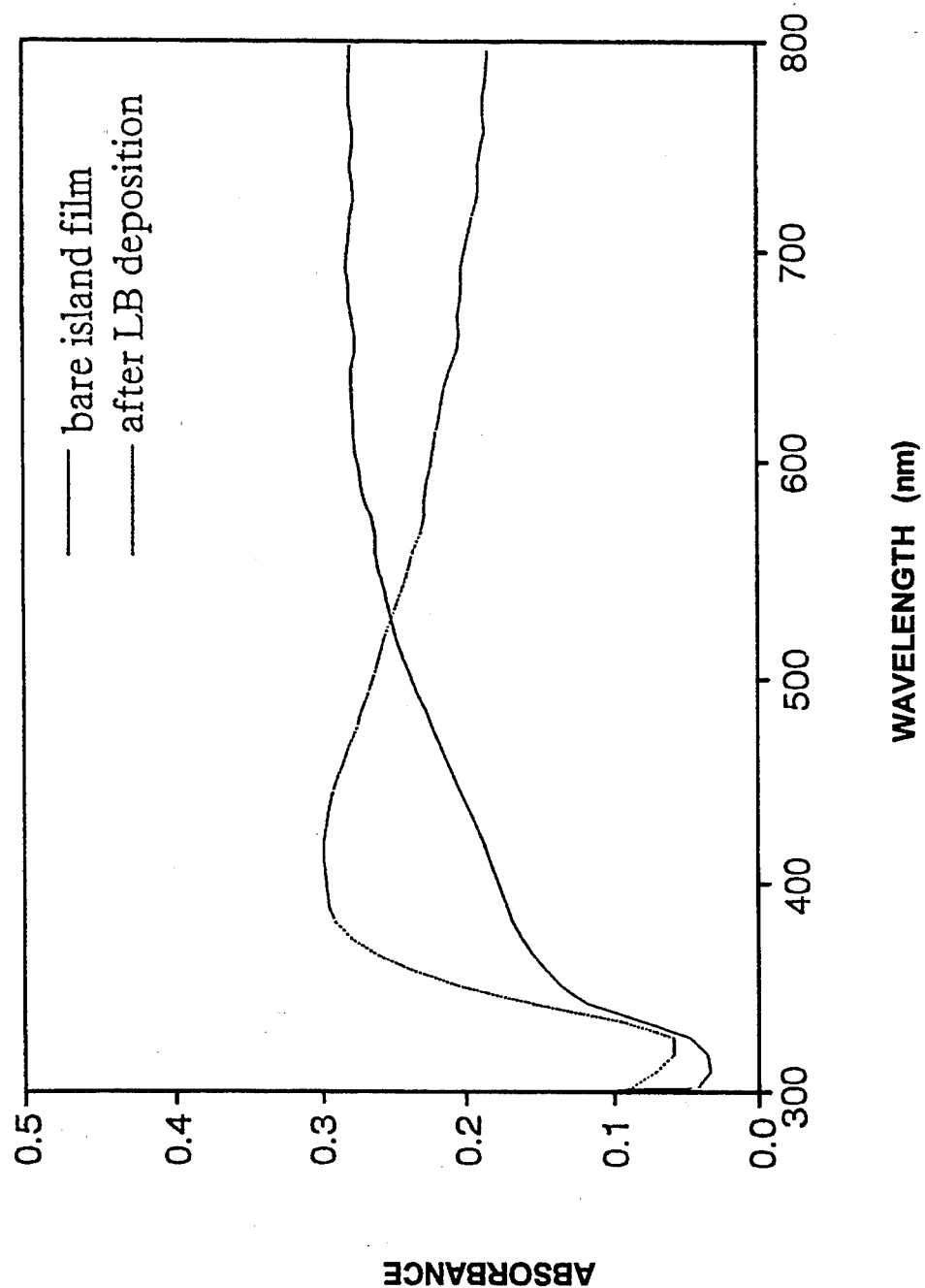
Figure 4C:
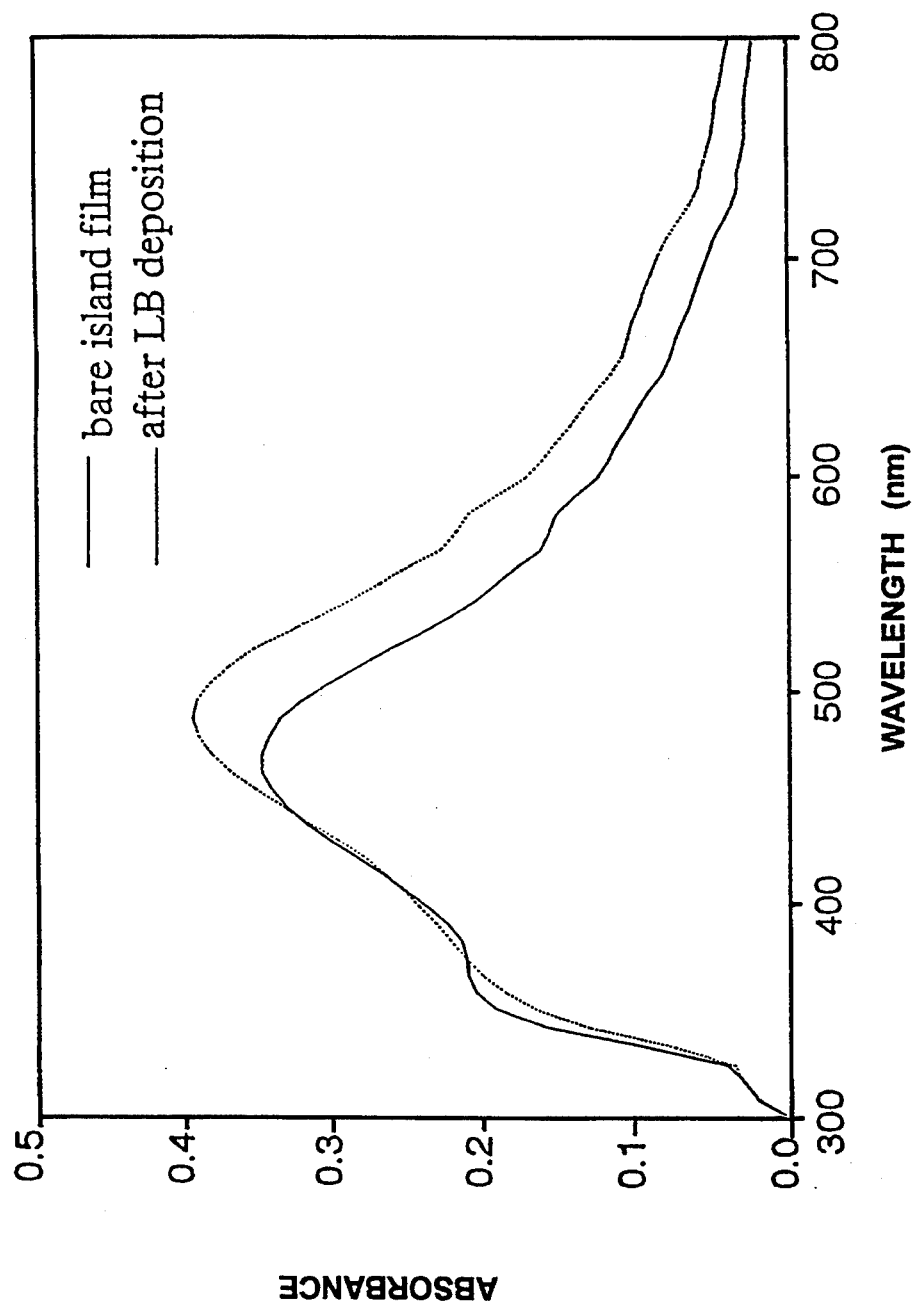
Figure 4D:
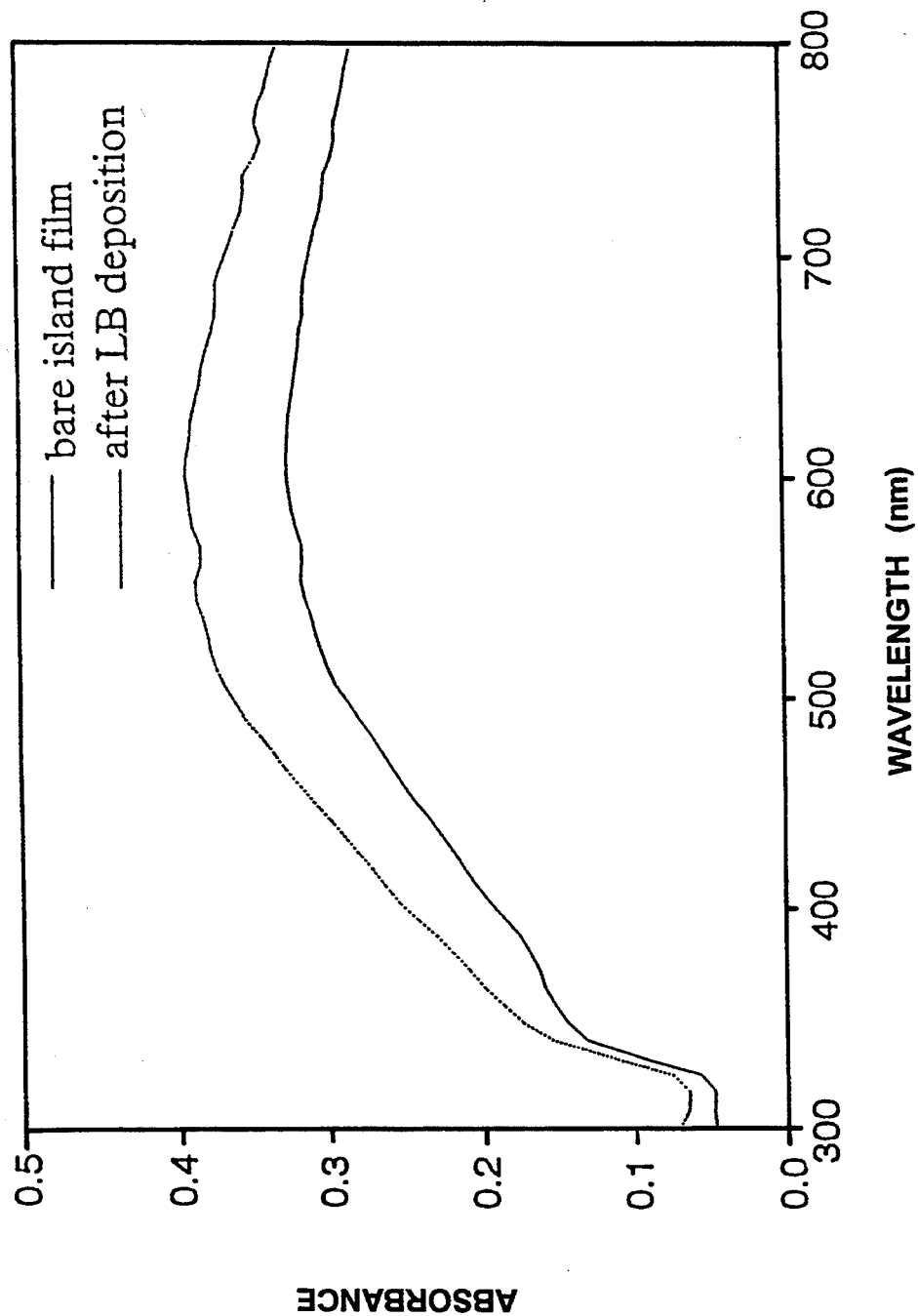

Silver island films were prepared by slow deposition of 40 Å (mass thickness) of silver onto a heated glass substrate either at room temperature or at 200° C. Absorption spectra of the unheated films exhibit a broad band (FIGS. 4a, 4b and 4d) extending from 320 to 800 nm which at times exhibited a band maximum at approximately 600 nm (FIG. 4d). The silver island film prepared on a heated substrate exhibited a relatively sharp absorption band centered at 475 nm with a shoulder at 320 nm (FIG. 4c).

Polarized absorption spectra of the silver island films show the presence of two bands, a sharp band at 330 nm present only in the parallel polarized spectra and a broader band centered at 475 nm for the heated film and between 600 to 700 nm for the unheated films present in both the parallel and perpendicular spectra. The polarized absorption response of these films is indicative of the presence of oblate silver island hemispheroids with a larger major/minor axis associated with the unheated silver island films.

The silver island films were classified as type A or B and subtype I or II based on the observed absorption response of the silver island films to LB deposition of the dye layer(s) and the adsorption band width and position after LB deposition. Type A films exhibited an overall shape change in the absorption band with the formation of a short wavelength peak while type B films maintained their general shape and exhibited an increase in absorbance and a shift to longer wavelength. Subtypes I and II correspond to silver island films which after LB deposition either do or do not respectively exhibited significant adsorption above 600 nm.

The deposition conditions, wettability and morphological characteristics of these silver island films are summarized in the table of FIG. 8.

Figure 5A:
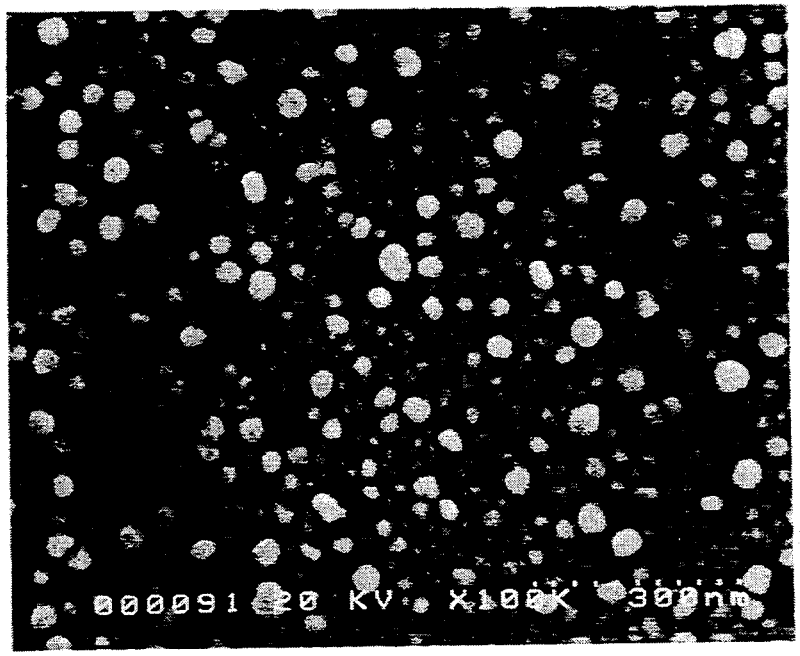
FIGS. 5a, 5b, 5c and 5d are scanning electron micrographs of silver island film types silver island film type A-I, silver island film type A-II, silver island film type B-I and silver island film type B-II respectively. All micrographs are at 100,000×
Figure 5B:
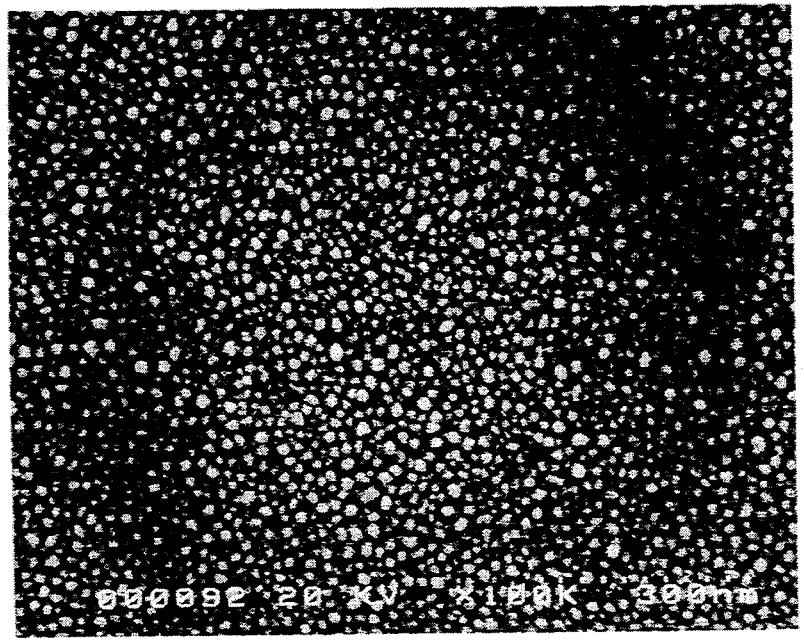
Figure 5C:
Figure 5D:
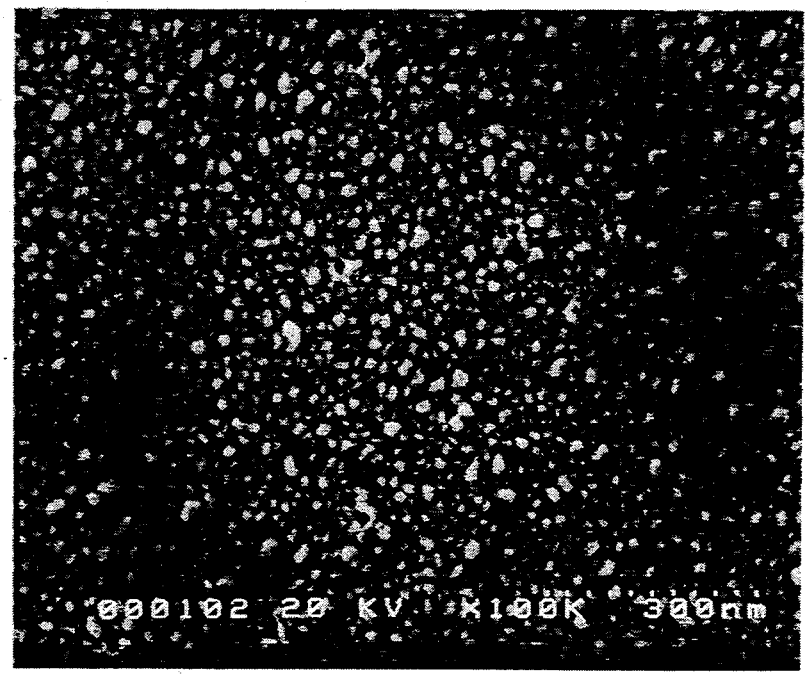

Scanning electron micrographs(SEM's) indicate that the average island diameter for type A films (FIG. 5a and 5b) is greater than 200 Å while for type B (FIGS. 5c and 5d) the average island diameter is less than 200 Å. Subtype I films (FIG. 5a and 5c) consist of well defined and isolated silver islands while subtype II films consist of poorly defined islands close contact with one another.

Monolayers of the mixed fluorophore BA films were deposited at a surface pressure of 33 mN/m which corresponds to the liquid condensed region of the pressure-area isotherm of behenic acid. A transfer ratio of 1 was obtained for all depositions on the glass, silver island and silvered surfaces indicating good transfer. The presence of 0.1 mM cadmium ion in the subphase results in a closely packed parallel arrangement of fatty acid ions (orthorhombic) associated with the counter cadmium ion, with less than 1% of the free acid remaining [7]. Ellipsometric measurements of the LB layers on the smooth silvered surfaces (assuming an isotropic refractive index of 1.50 [8]) provided a mean monolayer thickness of 30±1 Å which is slightly less than the expected thickness of 32.5 Å [9,10]. The orientations of the deposited fluorophore/BA films for the different substrates used are shown in FIG. 2 along with the approximate distances of the fluorophores from the substrate and air interfaces.

Figure 3A:
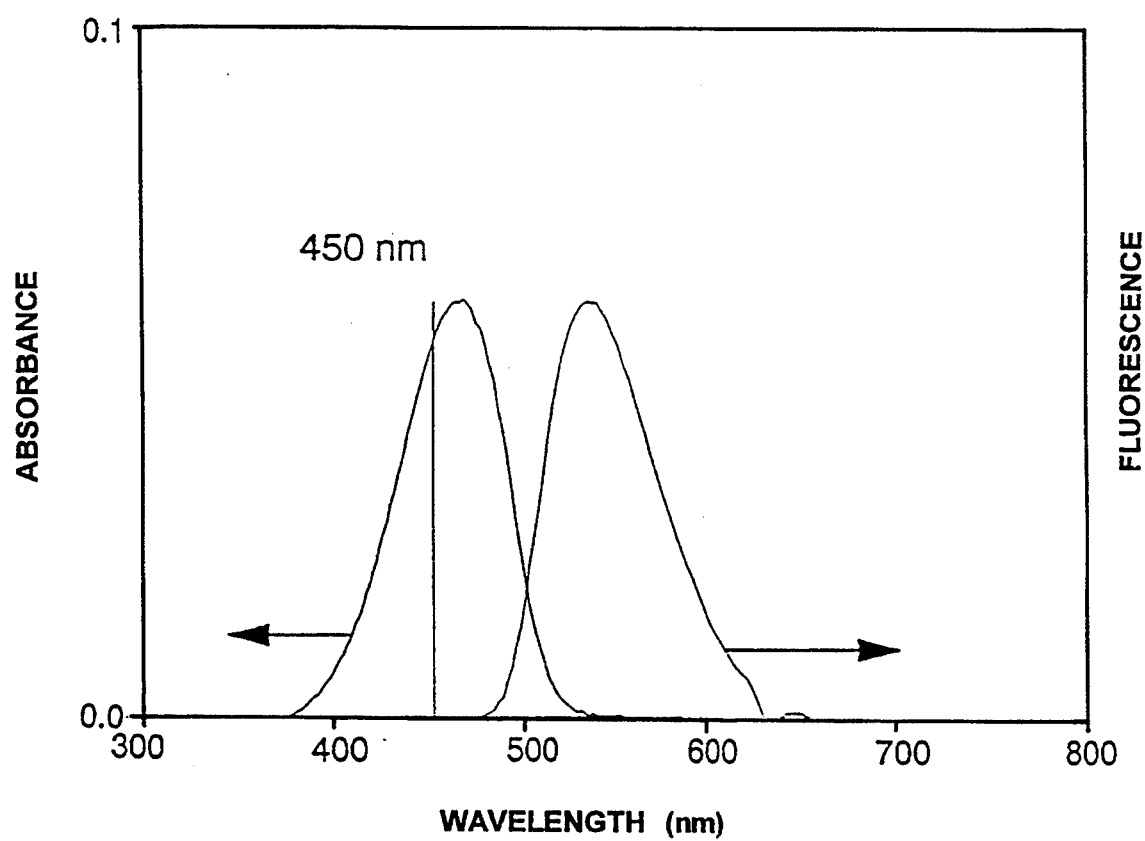
FIGS. 3a and 3b are graphs illustrating the absorption and fluorescence spectra of 30 μM NBD-PE and 30 μM TRITC-PE respectively in methanol
Figure 3B:
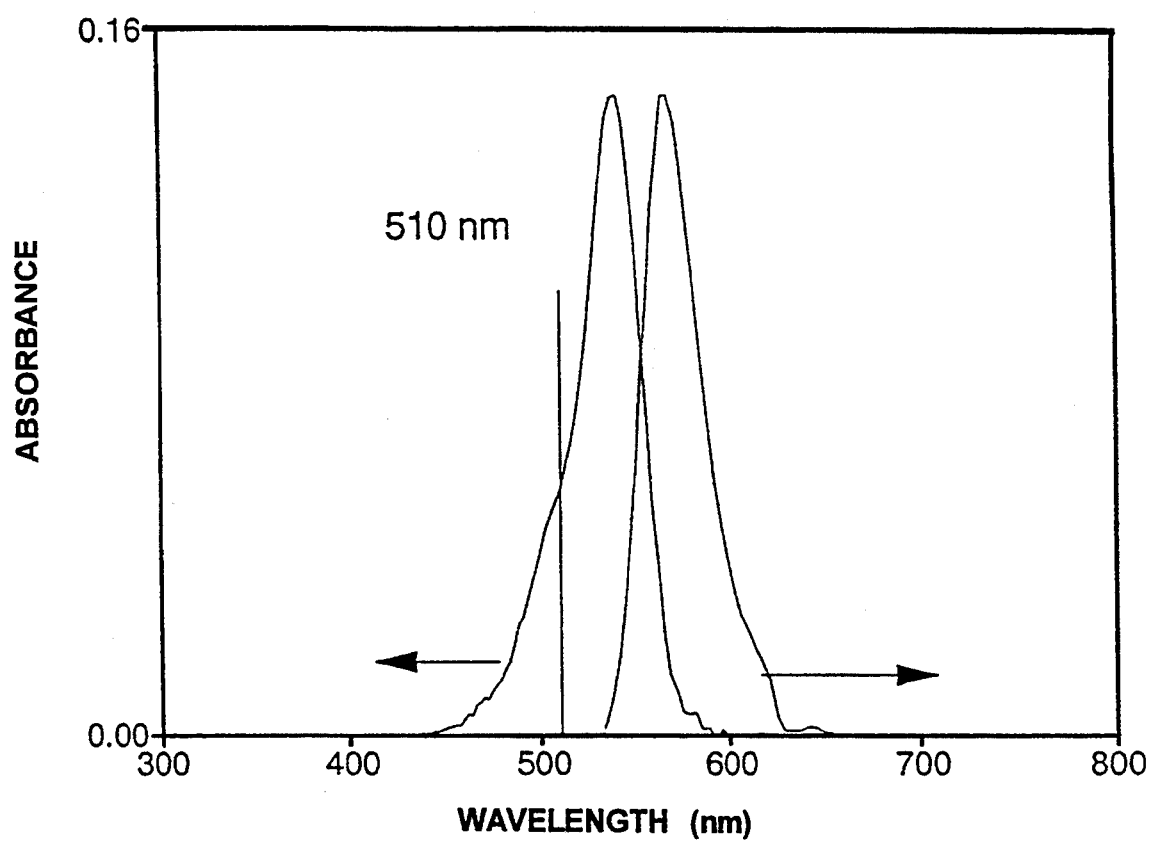

The absorption and fluorescence spectra of 30 μm NBD-PE and 30 μM TRITC-PE in methanol are shown in FIGS. 3a and 3b. Direct physical contact between the fluorophore and the silver island surface does not occur and as a result no significant perturbation of the electronic structure of the fluorophore is expected, hence the fluorescence spectra from the monolayers on the smooth silver and silver island surfaces are expected to be similar to those observed in methanol. This permitted the identification of spectral signals due to physical scatter at the solid surfaces to be distinguished from fluorescence.

Fluorescence measurements of the deposited mixed fluorophore behenic acid monolayers were carried out with an incident excitation angle of 60° and a collection angle of 30° with reference to the wafers normal. For the NBD-PE systems an excitation wavelength of 450 nm was used and the measured fluorescence intensity was integrated from 480 to 630 nm. For the TRITC-PE systems an excitation wavelength of 510 nm was used and the measured fluorescence intensity was integrated from 530 to 630 nm. The integrated fluorescence intensity of 0.1 and 1 mol % NBD-PE/BA layers deposited on silver island types A-II and B-I and a smooth silver film are summarized in FIG. 9.

No fluorescence (0.0±0.2) was observed for 0.1 and 0.5 mol % of TRITC-PE/BA deposited on silver island film types A-II, B-I, B-II and smooth silver films except for a small amount of fluorescence (1.0±0.5) for 0.5 mol % TRITC-PE/BA on silver island type A-I.

Figure 6:
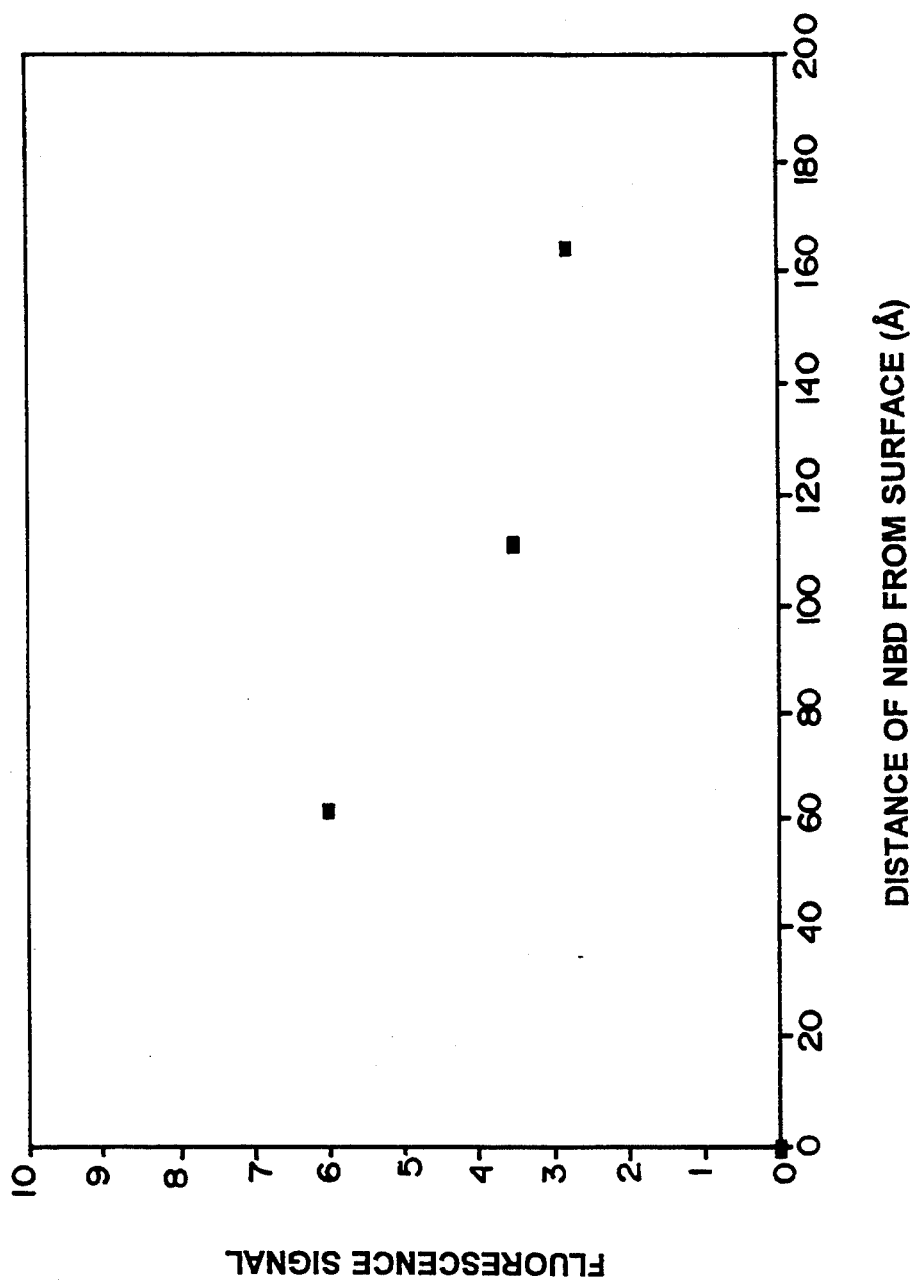
FIG. 6 is a graph illustrating the fluorescence distance response for an inverted bilayer of 1 mol % NBD-PE from silver island type B-I surface.

A series of wafers were prepared using pure BA layers as spacers to vary the distance between an inverted 1 mol % NBD-PE/BA bilayer from a silver island type B-I film surface. FIG. 6 shows the integrated fluorescence response as a function of distance.

Figure 7A:
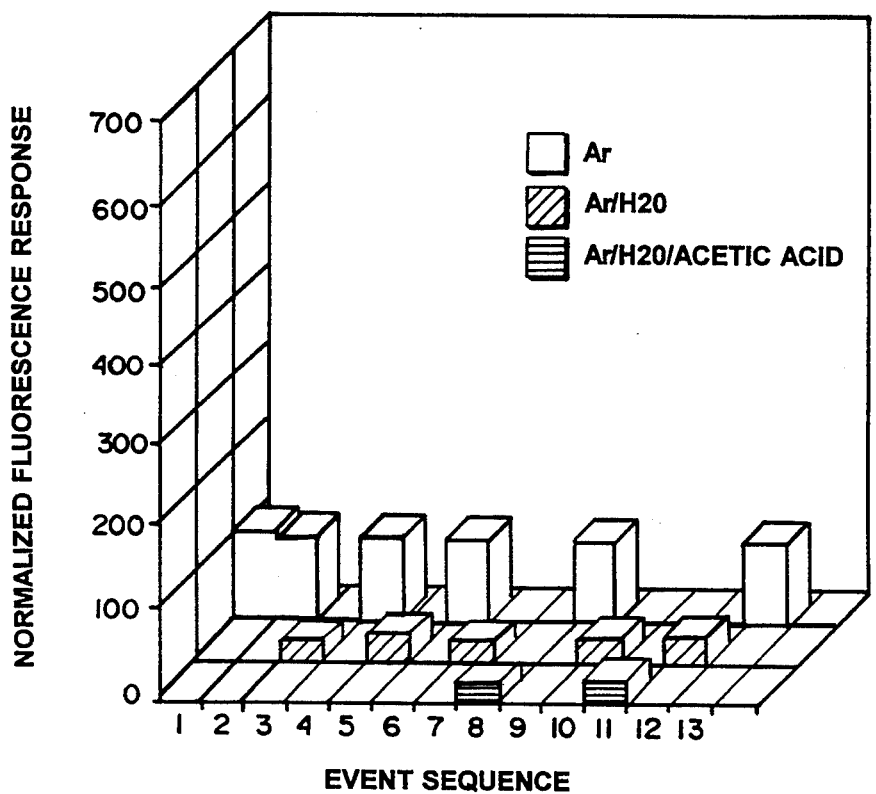
FIGS. 7a, 7b, 7c and 7d are block diagrams illustrating the fluorescence response of 1 mol % NBD-PE/BA monolayer on glass and a 1 mol % NBD-PE/BA inverted bilayer on silver island type A-II for exposure to dry argon, 30 ppt water and a mixture of 30 ppt and 0.5 ppt acetic acid vapour.
Figure 7B:
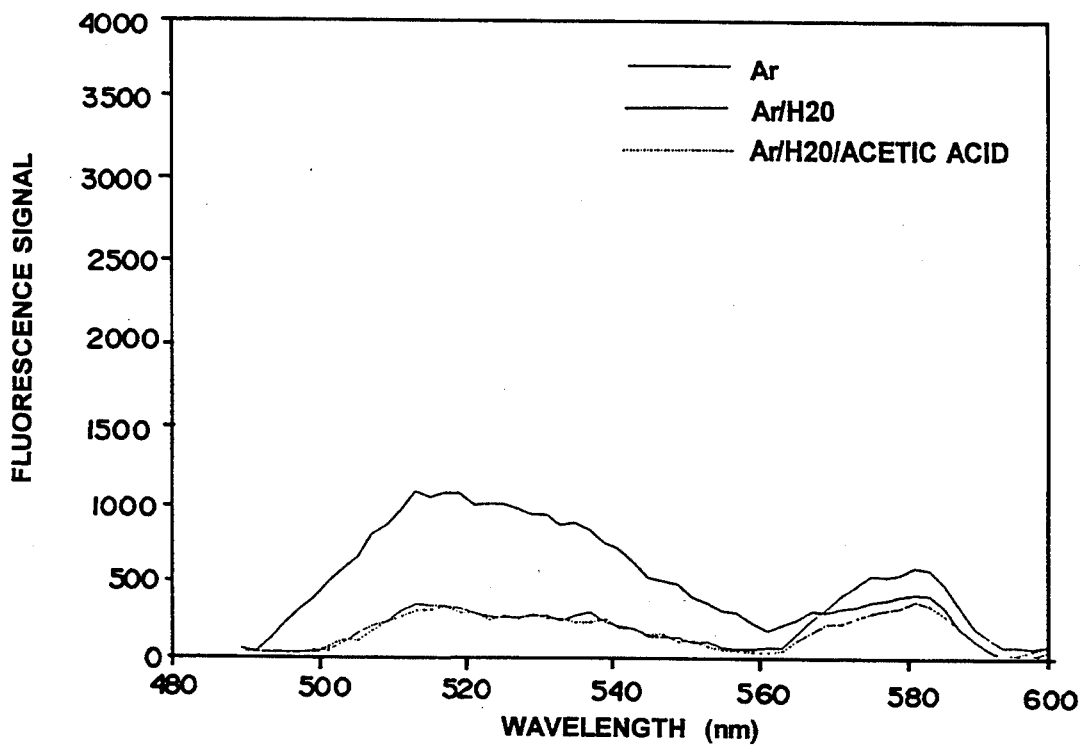
Figure 7C:
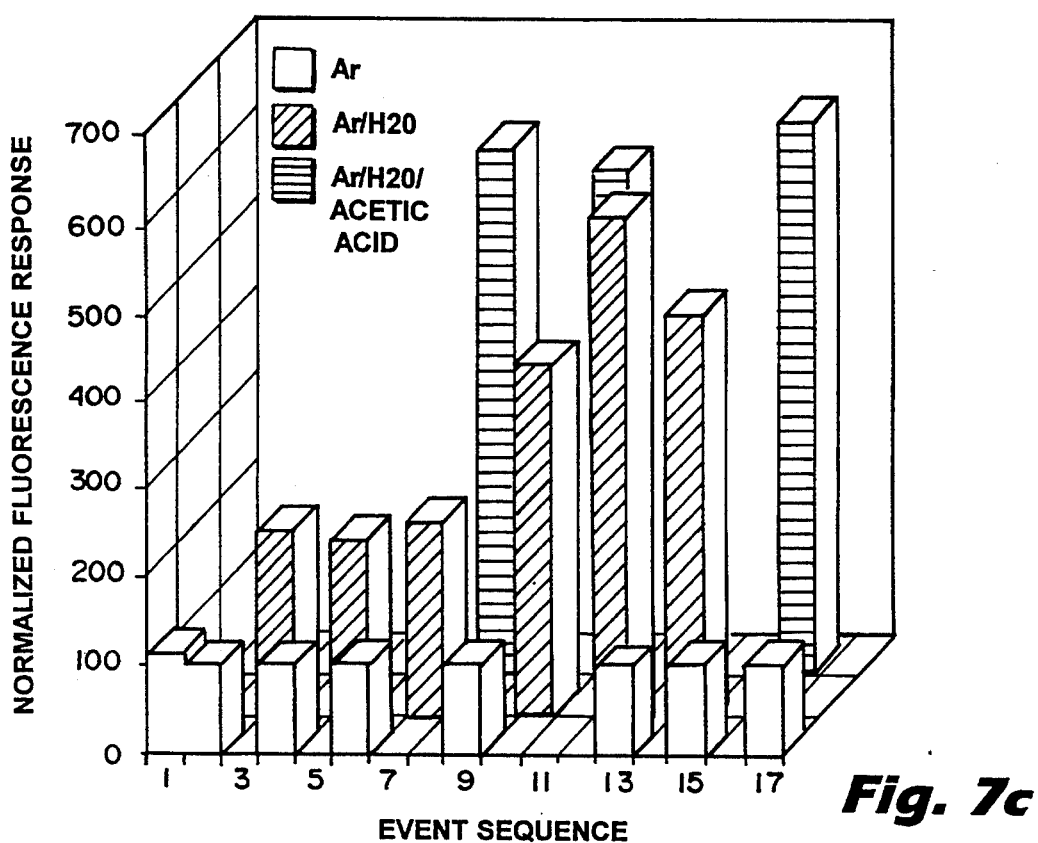
Figure 7D:
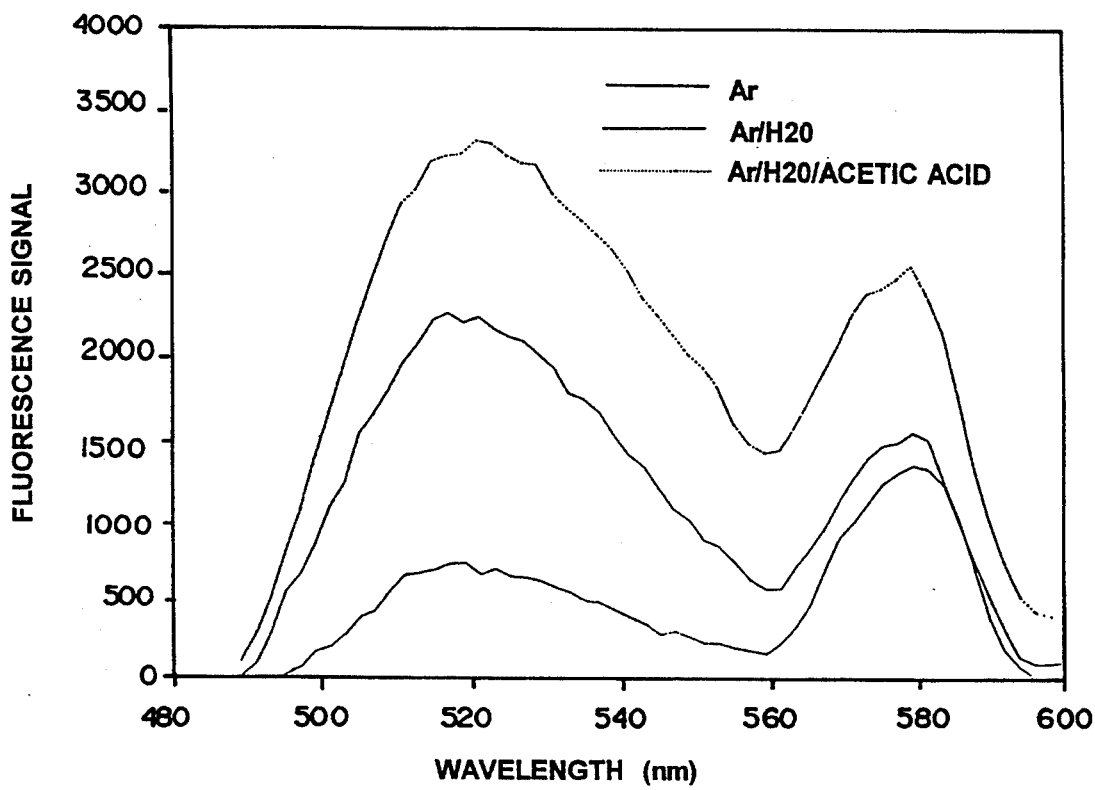

The integrated fluorescence response (493–560 nm) of a 1 mol % NBD-PE/BA monolayer on a glass surface and an inverted bilayer on a type A-II silver island surface for exposure to 30 ppt water vapour and a mixture of 30 ppt water and 0.5 ppt acetic acid vapour are shown in FIGS. 7a and 7c. The fluorescence response has been normalized for each sample to the preceding argon signal in order correct for any additional scattering resulting from structural changes in the BA layers. FIGS. 7b and 7d show the corrected spectra (background eliminated) for the wafers exposed to dry argon, 30 ppt water vapour and a mixture of 30 ppt water and 0.5 ppt acetic acid vapour. A second spectral band centered at 580 nm is attributed to physical scatter.

DISCUSSION

Enhancing the local electric field intensity at the excitation and emission wavelengths of a fluorophore will lead to enhanced absorption and radiative decay rates. Since NBD-PE and TRITC-PE are relatively high quantum yield fluorophores in solution the major source of fluorescence enhancement is expected to arise as a result of an enhanced absorption rate. For a smooth silver film an incident angle of 60° results in a maximum normal surface field intensity enhancement of 3 fold. Experimentally no fluorescence was observed on the smooth silver films. The enhanced absorption rate of the fluorophore has been offset by an increased non-radiative decay rate as a result of fast non-radiative energy transfer to the metal film involving the generation of non-radiative electron-hole pairs and surface plasmons[11,12].

The absorption and fluorescence emission spectra of NBD-PE and TRITC-PE shown in FIGS. 3a and 3b overlap with the absorption bands of the metal island films shown in FIG. 4, hence the fluorophores will experience an enhanced electric field intensity over the incident field intensity at the excitation and emission wavelengths. Using equation 5 an approximation of the field intensity enhancement at the surface of these films can be calculated for the excitation and emission wavelengths used, and these results are summarized in FIG. 10.

The calculated field intensity enhancement at the excitation wavelength is greater for silver island type B indicating that a larger fluorescence signal should be observed for these films. Experimentally a larger fluorescence signal is observed for NBD-PE/BA on type A islands than on type B islands. In fact the fluorescence of the NBD-PE/BA system on type B silver islands is completely quenched at a concentration of 0.1 mol % with only a small amount of fluorescence observed at 1 mol %.

The fluorescence spectrum (FIG. 3) of NBD-PE and TRITC-PE overlaps to significant degree with all the absorption spectra of the silver island films (FIG. 4), indicating that the excited fluorophores can relax by dipole-dipole coupling with a metal particle involving excitation of a dipolar surface plasmon. Whether the subsequently excited dipolar surface plasmon relaxes radiatively or non-radiatively depends on the particle size. Type A islands have a larger average island diameter than type B islands indicating that the former silver islands have a higher radiative decay rate and hence a larger observed fluorescence signal which is observed experimentally for both the NBD-PE/BA and TRITC-PE/BA films.

Field intensity enhancement associated with the silver island film according to theory is a long range effect compared to the quenching of fluorescence by the metal island which is a short range effect. Consequently, as the fluorophore is moved away from the surface the fluorescence should increase to some maximum value and then decrease with increasing distance. The fluorescence distance response of an inverted 1 mol % NBD-PE/BA bilayer on a silver island type B-I film (FIG. 6) shows a optimum intermediate distance at 60 Å which compares favourably with the reported optimum distance for the high quantum yield fluorophore rhodamine 6G of 50 Å [13]. The fluorescence signal increases with increasing distance from 100 Å to 500 Å as non-radiative energy losses from the flourophore to non-radiative surface modes decreases with increasing distance.

The fluorescence response generated by exposure of a monolayer of 1 mol % NBD-PE/BA on a glass surface and an inverted bilayer on a silver island type A-II surface to argon saturated with water and acetic acid is shown in FIGS. 7a–d. These surfaces are chemically selective to alterations of hydronium ion activity. Both surfaces responded in a reproducible and reversible manner which indicates that an equilibrium response is reached within seconds to minute, as expected for very thin chemically selective coatings. For the glass surface, exposure to water or an acetic acid/water vapour mixture results in a quenching of fluorescence with no preferential response when acetic acid is present. However, for the silver island substrate exposure to water vapour results in an increase in fluorescence which is significantly enhanced when acetic acid is present. Purging the system with dry argon and subsequent exposure to water vapour results in a two-fold enhancement of fluorescence. This suggests that acetic acid has partitioned into the bilayer in an non-reversible manner thereby sensitizing it to the presence of water. The partitioned acetic acid in the bilayer may provide additional regions of hydration due to its ability to hydrogen bond, which consequently increases structural change in the bilayer.

Results have been presented indicating the measurement of fluorescence from the relatively high quantum yield fluorophores NBD and TRITC in close proximity to metal island films consisting of oblate islands with an average diameter larger than 200 Å. Very little or no fluorescence was observed for fluorophores adjacent to smooth metal films or silver island films with an average diameter less than 200 Å. The fluorescence response of a 1 mol % NBD-PE/BA bilayer deposited on a silver island surface to exposure to 30 ppt water vapour and a mixture of 30 ppt water and 0.5 ppt acetic acid vapour indicated that these systems can be used to transduce structural changes in an inverted bilayer due to the selective binding of an analyte, and this response is amplified six fold compared to a glass based system.

REFERENCES

1 A. Ulman, *An Introduction to Ultrathin Organic Films*, Academic Press Inc., San Diego, Calif., 1991

2 P. Rouard and A. Meesen, in E. Wolf (ed.) *Optical Properties of Thin Metal Films* in Progress in Optics, Vol. 15, 1977, pp77–137

3 D. A. Weitz, S. Garoff, J. I. Gersten and A. Nitzan, The enhancement of Raman scattering, resonance Raman scattering and fluorescence from molecules adsorbed on a rough silver surface, *J. Chem. Phys.*, 78(9) (1983) 5324–5338.

4 D. A. Weitz, S. Garoff and T. J. Gramila, Excitation spectra of surface-enhanced Raman scattering on silver island films, Opt. Let., 7(4) (1982) 168–170

5 A. Wokaun, H. P. Lutz, A. P. King, U. P. Wild, R. R. Ernst, Energy transfer in surface enhanced luminescence, *J. Chem. Phys.* 79(1) (1983) 509–514

6 J. Gerstein, A. Nitzan, *J. Chem. Phys.* Spectroscopic properties of molecules interacting with small dielectric particles, 75(3) (1981), 1139–1152

7 J. F. Rabolt, F. C. Burns, N. E. Schlotter and J. D. Swalen, Anisotropic orientation of monolayers by infrared spectroscopy, *J. Chem Phys.* 78(2) (1983) 946–952

8 I. Pockrand, J. D. Swalen, J. G. Gordon II and M. R. Philpott, Surface plasmon spectroscopy of organic monolayer assemblies, Surf. Sci. 74 (1977) 237–244

9 Based on adding 6.0 Å to the accepted length of cadmium arachidate of 26.8 Å monolayer 10 J. D. Brennan, R. S. Brown, S. F. Ferraro and U. J. Krull, Hydronium ion sensitivity of surface stabilized stearic acid membranes prepared by Langmuir-Blodgett monolayer transfer, Thin Solid Films, 203 (1991) 173–184.

11 W. H. Weber and E. F. Eagan. Energy transfer from an excited dye molecule to the surface plasmon of an adjacent metal, Opt. Lett., 4(1979) 236

12 I. Pockrand, A. Brillante and D. Mobius, Non-radiative decay of excited molecules near a metal surface, Chem. Pys. Let., 69(3) (1980) 499

13 F. R. Assenegg, A. Leitner, M. E. Lippitsch, H. Reinisch and M. Riegler, Novel aspects of fluorescence lifetime for molecules positioned close to metal surfaces, Surf. Sci. 189/190 (1987) 935–945

We claim:

1. A fluorescently based chemical sensor comprising a substrate, a metal island film deposited on said substrate, and an ordered monolayer or multilayer chemically-selective film less than 200 Å thick which contains fluorophore deposited on said metal, whereby the fluorescence is enhanced and/or changed by electric field interactions with the metal islands.

2. A chemical sensor as claimed in claim 1 wherein said metal island film consists of a metal or metal alloy whose dielectric constant in the visible region of the electromagnetic spectrum is such that $\epsilon_1<0, \epsilon_2>0$ and $|\epsilon_1|>\epsilon_2$ and $(\epsilon_1+i\epsilon_2)$ is the complex dielectric constant of bulk silver.

3. A chemical sensor as claimed in claim 2 wherein said metal island film is selected from the group consisting of a silver island film, gold island film, indium island film or alloys of mixtures of said metals.

4. A chemical sensor as in claim 3 wherein said fluorophore is selected from fluorophores having an absorption band which overlaps that of the metal island film.

5. A chemical sensor as claimed in claim 4 wherein said fluorophore film is located within 60 Å of the metal island surface.

6. A chemical sensor as claimed in claim 5 wherein said fluorophore is a dipcast film.

7. An optical chemical sensor comprising a substrate, a metal island film deposited on said substrate and a fluorophore film deposited on said metal island film, whereby fluorescence enhancement of said fluorophore is achieved when an excitation wavelength overlaps the absorption band of both the fluorophore and metal island film, said metal island film is selected from the group consisting of a silver island film, gold island film, indium island film or alloys of mixtures of said metals whose dielectric constant in the visible region of the electromagnetic spectrum is such that $\epsilon_1<0, \epsilon_2>0$ and $|\epsilon_1|>\epsilon_2$ and $(\epsilon_1+i\epsilon_2)$ is the complex dielectric constant of bulk silver, the fluorophore is selected from fluorophores having an absorption band which overlaps that of the metal island film, the fluorophore film is located within 60 Å of the metal island surface and wherein said enhanced or changed fluorescence is achieved by direct structural alteration of the fluorophore.

8. An optical chemical sensor comprising a substrate, a metal island film deposited on said substrate and a fluorophore film deposited on said metal island film, whereby fluorescence enhancement of said fluorophore is achieved when an excitation wavelength overlaps the absorption band of both the fluorophore and metal island film, said metal island film is selected from the group consisting of a silver island film, gold island film, indium island film or alloys of mixtures of said metals whose dielectric constant in the visible region of the electromagnetic spectrum is such that $\epsilon_1<0, \epsilon_2>0$ and $|\epsilon_1| \epsilon_2$ and $(\epsilon_1+i\epsilon_2)$ is the complex dielectric constant of bulk silver, the fluorophore is selected from fluorophores having an absorption band which overlaps that of the metal island film, the fluorophore film is located within 60 Å of the metal island surface and wherein said enhanced or changed fluorescence is achieved by a physical alteration of the environment surrounding the fluorophore.

* * * * *